US011207371B2

(12) United States Patent
Kessoku et al.

(10) Patent No.: US 11,207,371 B2
(45) Date of Patent: Dec. 28, 2021

(54) COMPOSITION FOR IMPROVING OR PREVENTING NONALCOHOLIC FATTY LIVER

(71) Applicants: KOHJIN LIFE SCIENCES CO., LTD., Tokyo (JP); PUBLIC UNIVERSITY CORPORATION YOKOHAMA CITY UNIVERSITY, Yokohama (JP); KYOTO PREFECTURAL PUBLIC UNIVERSITY CORPORATION, Kyoto (JP); SAGA UNIVERSITY, Saga (JP)

(72) Inventors: Takaomi Kessoku, Yokohama (JP); Atsushi Nakajima, Yokohama (JP); Yoshio Sumida, Kyoto (JP); Yuichiro Eguchi, Saga (JP); Susumu Saito, Chiyoda-ku (JP); Yusuke Sauchi, Chiyoda-ku (JP)

(73) Assignees: KOHJIN LIFE SCIENCES CO., LTD., Tokyo (JP); PUBLIC UNIVERSITY CORPORATION YOKOHAMA CITY UNIVERSITY, Yokohama (JP); KYOTO PREFECTURAL PUBLIC UNIVERSITY CORPORATION, Kyoto (JP); SAGA UNIVERSITY, Saga (JP)

( * ) Notice: Subject to any disclaimer, the term of this patent is extended or adjusted under 35 U.S.C. 154(b) by 0 days.

(21) Appl. No.: 16/889,367

(22) Filed: Jun. 1, 2020

(65) Prior Publication Data
US 2020/0289605 A1    Sep. 17, 2020

Related U.S. Application Data

(62) Division of application No. 16/232,747, filed on Dec. 26, 2018, now abandoned, which is a division of application No. 15/555,901, filed as application No. PCT/JP2016/056341 on Mar. 2, 2016, now abandoned.

(30) Foreign Application Priority Data

Mar. 3, 2015    (JP) ................. 2015-041317

(51) Int. Cl.
*A61K 38/00* (2006.01)
*A61K 38/06* (2006.01)
*A61P 1/16* (2006.01)

(52) U.S. Cl.
CPC ............ *A61K 38/063* (2013.01); *A61K 38/00* (2013.01); *A61P 1/16* (2018.01)

(58) Field of Classification Search
None
See application file for complete search history.

(56) References Cited

U.S. PATENT DOCUMENTS

2011/0003757 A1    1/2011    Kurosaki et al.

FOREIGN PATENT DOCUMENTS

| JP | 2006-199708 A | 8/2006 |
| WO | 2009/096455 A1 | 8/2009 |

OTHER PUBLICATIONS

Nonalcoholic steatohepatitis (NASH), Merck Manual, accessed Jul. 29, 2016 at URL merckmanual.com, pp. 1-3 (Year: 2016).*
Chalasani et al., "The diagnosis and management of non-alcoholic fatty liver disease: practice Guideline by the American Association for the Study of Liver Diseases, American College of Gastroenterology, and the American Gastroenterological Association," Chalasani et al., Hepatol. 55:2005-2023 (2012)) (Year: 2012).*
Schaffler et al., "Mechanisms of Disease: adipocytokines and visceral adipose tissue—emerging role in nonalcoholic fatty liver disease" Nat. Rev. Gastroenterol. Hepat. 2:273-280 (2005) (Year: 2005).*
Shimada et al., "Usefulness of a Combined Evaluation of the Serum Adiponectin Level, HOMA-IR, and Serum Type IV Collagen 7S Level to Predict the Early Stage of Nonalcoholic Steatohepatitis,"Am. J. Gastroenterol. 102:1931-1938 (2007) (Year: 2007).*
Yoneda et al., "Noninvasive assessment of liver fibrosis by measurement of stiffness in patients with nonalcoholic fatty liver disease (NAFLD)," Digestive and Liver Disease 40:371-378 (2008) (Year: 2008).*
Pizzorno, "Glutathione!," Integrative medicine 13:8-12 (Feb. 2014) (Year: 2014).*
Yang, Zhao Xia et al., "Effect of Cordyceps Sinensis and Reduced Glutathione on Experimental Mouse Model With Non-Alcoholic Fatty Liver Disease" Acta Academiae Medicinae Militaris Tertiae, (2007), vol. 29, No. 22, pp. 2176-2178.
Li, Xiao Pei et al., "Effects of Reduced Gluthione and Polyene Phosphatidylcholine on Nonalchoholic Steatohepatisis in Rats" Chinese Jounral of Gastroenterology and Hepatology, (2011), vol. 20, No. 7, pp. 610-613.
Rana, S Vs, "Lipotropic Effects of Zinc, Vitamin B12, and Glutathione on the Fatty Liver of Rat", A Histochemical Study, Mikroskopie, (1981), vol. 38, pp. 294-300.

(Continued)

*Primary Examiner* — Julie Ha
*Assistant Examiner* — Kristina M Hellman
(74) *Attorney, Agent, or Firm* — Oliff PLC

(57) ABSTRACT

An object of the present invention is to provide a composition for preventing or improving fat deposition on the liver in spite of the alcohol intake history of a level that a liver disease is not caused. The inventors found that glutathione has an effect of preventing or improving fat deposition on the liver, which is not caused by alcohol, and completed the present invention. Among nonalcoholic fat diseases, the present invention is particularly effective in an early stage of the treatment or in a case where treatment for another disease is not performed.

5 Claims, 5 Drawing Sheets

(56) References Cited

OTHER PUBLICATIONS

Figure 1:
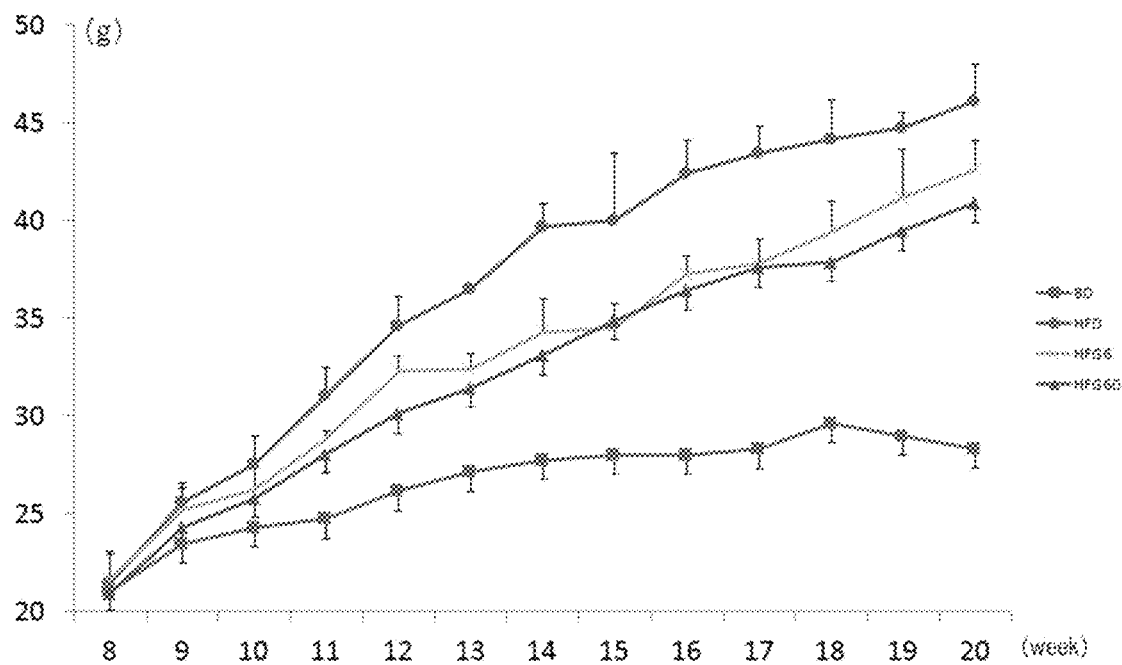

Shon, Mi Yae et al., "Protective Effect of Administrated Glutathione-Enriched *Saccharomyces cerevisiae* FF-8 Against Carbon Tetrachloride (CC14)-Induced Hepatotoxicity and Oxidative Stress in Rats", Food Science and Biotechnology, (2007), vol. 16, No. 6, pp. 967-974.
Okuno, Fumio et al., "Shibokan", Clinical Drug Intelligence, (1985), vol. 4., No. 4 (Whole No. 18), p. 69 (429)—72 (432).
May 24, 2016 Search Report issued in International Patent Application No. PCT/JP2016/056341.
May 24, 2016 Written Opinion issued in International Patent Application No. PCT/JP2016/056341.
Li et al., Chinese Journal of Gastroenterology and Hepatology 20(7): 610-613, (2011)—translation pp. 1-16, translated Aug. 2018.
Yang et al., Acta Academie Medicinae Militaris Tertiae 29(22): 2176-2178 (2007)—translation pp. 1-13, translated Aug. 2018.
Mo et al., "treating 46 cases of non-alcoholic fatty liver using integrative Chinese and Western Medicine," Journal of Practical Traditional Chinese Internal Medicine 25(3): 75-76 (2011).
Mo et al., Journal of Practical Traditional Chinese Internal Medicine 25(3):75-76(2011)—transltation pp. 1-10 translated Aug. 2018.

* cited by examiner

COMPOSITION FOR IMPROVING OR PREVENTING NONALCOHOLIC FATTY LIVER This application is a divisional application of U.S. patent application Ser. No. 16/232,747 filed on Dec. 26, 2018, which in turn is a divisional application of U.S. patent application Ser. No. 15/555,901, filed Sep. 5, 2017, which is a U.S. national stage entry of PCT/JP2016/056341, filed Mar. 2, 2016, which claims priority to JP 2015-041317, filed Mar. 3, 2015. The disclosures of each of the above are hereby incorporated by reference in their entirety.

TECHNICAL FIELD

The present invention relates to a composition for preventing or improving nonalcoholic fatty liver in which fat is deposited on a liver in spite of the alcohol intake history of a level that a liver disease is not caused.

BACKGROUND ART

Increase of diabetes, fatty liver, cancer, cardiac disease and the like as a lifestyle related disease has been problematic. Fat may be deposited on the liver and cause a hepatic disorder in spite of the alcohol intake history of a level that a liver disease is not caused. The cause is obesity, diabetes, hyperlipidemia or the like, but factors involved in the pathogenesis are diverse and there is no established therapy. The disease state of such nonalcoholic fatty liver disease (NAFLD) may proceed to the nonalcoholic steatohepatitis (NASH), hepatic cirrhosis or liver cancer. The nonalcoholic fatty liver disease often comes with insulin resistance, obesity, diabetes and hyperlipidemia. With respect to the nonalcoholic fatty liver disease, exercise or dietetic therapy is usually performed. In addition, with respect to the nonalcoholic fatty liver disease, treatment with a medicament or dietetic therapy using nutritional supplementary food or the like is required in addition to exercise, dietetic therapy and the like. Furthermore, nonalcoholic steatohepatitis is likely to develop to hepatic cirrhosis or liver cell cancer, and thus needs more active treatment and the like.

In a nonalcoholic fatty disease, treatment for diabetes and the like may be performed together, and thus it is also necessary to improve the nonalcoholic fatty liver disease while not inhibiting treatment of the complication.

Therefore, functional food, supplement and the like having therapeutic effects for the nonalcoholic fatty liver disease are also desired, which have superior effects without concern of the side reactions, and are easy to take, and can be taken for a long time.

On the other hand, glutathione is a tripeptide consisting of amino acids of cysteine, glutamic acid and glycine, and is known as a drug improving detoxication of the liver.

However, it has been not known that glutathione is effective for the nonalcoholic fatty liver disease.

CITATION LIST

Patent Literature

Patent Literature 1: WO 2009/096455 A
Patent Literature 2: JP 2006-199708 A

SUMMARY OF INVENTION

Technical Problem

An object of the present invention is to provide a composition for preventing or improving fat deposition on the liver in spite of the alcohol intake history of a level that a liver disease is not caused.

Solution to Problem

The present inventors found that glutathione has an effect of preventing or improving fat deposition on the liver, which is not caused by alcohol, and completed the present invention.

The present inventions are as follows:
(1) A composition for improving a nonalcoholic fatty liver disease, including glutathione as an active ingredient;
(2) A composition for preventing a nonalcoholic fatty liver disease, including glutathione as an active ingredient;
(3) The composition according to (1) or (2), wherein the nonalcoholic fatty liver disease is a disease developed with nonalcoholic fatty liver only;
(4) The composition according to (1) or (2), wherein the nonalcoholic fatty liver disease is a disease not complicated with diabetes;
(5) The composition according to (1) or (2), wherein the nonalcoholic fatty liver disease is a disease having low liver stiffness; and
(6) The composition according to (1) or (2), wherein the nonalcoholic fatty liver disease is a disease having a glycosylated hemoglobin (HbA1c) of 6.5% or less.

Advantageous Effects of Invention

The composition of the present invention can be used effectively in order to improve fatty liver by reducing fat deposition on the liver with respect to nonalcoholic fatty liver, and further can suppress development to hepatic disorder. Therefore, the agent for suppressing fat deposition on the liver, and the agent for improving fatty liver of the present invention further have actions of preventing or improving development to hepatic cirrhosis, hepatitis and liver cancer based on the actions described above.

The composition of the present invention can be used effectively for a patient who is in an early stage of nonalcoholic fatty liver, particularly who is in mild disease state or does not have a metabolic disorder such as high blood pressure, hyperlipidemia or impaired glucose tolerance, a patient who has low liver stiffness, and a patient who does not have disease other than fatty liver. In these cases, the present invention is also effective for a disease that is not affected with meal, exercise therapy and the like.

DESCRIPTION OF EMBODIMENTS

Hereinafter, the present invention will be described in detail.

The nonalcoholic fatty liver disease (NAFLD) in the present invention means a disease leading to a hepatic disorder due to abnormal buildup of fat in a liver cell in spite of the alcohol intake history of a level that a liver disease is not caused, and a condition of likely leading to such hepatic disorder, and includes nonalcoholic simple fatty liver and nonalcoholic steatohepatitis. Generally, the nonalcoholic fatty liver disease (NAFLD) in the present invention represents the disease state where fat is deposited in a liver cell and a hepatic disorder is caused in spite of 20 g or less of the alcohol intake amount per one day.

Improvement of nonalcoholic fatty liver in the present invention indicates no deterioration of the liver function. In addition, improvement of nonalcoholic fatty liver in the present invention indicates therapeutic effects for a disease such as acute hepatitis, liver failure, chronic hepatitis, fatty liver and hepatic cirrhosis. Specifically, improvement of nonalcoholic fatty liver in the present invention indicates, for example, prevention for fat deposition on the liver, or suppression of increase or decrease in ALT (alanine aminotransferase), which is an item for clinical examination of the liver function. The prevention of nonalcoholic steatohepatitis in the present invention indicates suppression of increase or decrease in ALT, which is an item for clinical examination of the liver function.

In addition, among the nonalcoholic fatty liver diseases described above, the present invention is particularly effective in a case where fatty liver only is developed, in a case where diabetes is not developed (complicated), in a case where liver stiffness is low, or in a case where hepatic cirrhosis is not developed. Particularly, the present invention is effective in the case of treating, improving or preventing the nonalcoholic fatty liver disease only. Even in a case where diabetes is developed, the present invention is effective in a case where liver stiffness is low, and in a case where diabetic treatment is not performed.

Development of nonalcoholic fatty liver only in the present invention represents development of fatty liver only diagnosed as nonalcoholic fatty liver in an ordinary diagnosis. Generally, the development of nonalcoholic fatty liver only in the present invention represents the state of a level that fat is deposited on the liver with abdominal ultrasonography diagnosis, pictorial diagnosis and the like, and abnormality is recognized in ALT, which is an examination item of fatty liver, but a normal value or no need of treatment is determined in other examination items.

The patient not developed with diabetes in the present invention refers to a patient having a glycosylated hemoglobin (HbA1c) concentration of 6.5% or less (NGSP value). In addition, even though the glycosylated hemoglobin concentration is 6.5% or more, the present invention is effective in a case where treatment of diabetes is not performed.

The glycosylated hemoglobin is obtained by blood examination, and thus refers to the ratio of HbA1c occupying the total hemoglobin.

The present invention is also effective in the case of not being complicated with high blood pressure or hyperlipidemia.

Herein, the high blood pressure refers to a patient who has a systolic blood pressure (maximal high blood pressure) of 140 mmHg or more and a diastolic blood pressure (minimal blood pressure) of 90 mmHg or more. The hyperlipidemia refers to a patient who has high lipids, specifically cholesterol and neutral fat (representative one is triglyceride) in the blood, and generally a patient who has (1) hypercholesterolemia (total cholesterol value in the blood: 220 mg/dL or more), (2) a disease of high LDL cholesterol in the blood (low density lipoprotein (LDL) in the blood: 140 mg/dL or more), (3) a disease of low HDL cholesterol in the blood (HDL in the blood: less than 40 mg/dL), (4) a disease of high triglyceride in the blood (high triglyceride in the blood: 150 mg/dL or more). A patient called the reserve for a disease of high blood pressure or hyperlipidemia is also encompassed in the present invention.

The disease having low liver stiffness in the present invention refers to a disease corresponding to any one of the followings. However, the disease having low liver stiffness is not limited thereto, and the present invention is also effective for a disease having low liver stiffness diagnosed by other methods.

(1) Measurement value of Type IV collagen (Type IV collagen 7S domain) in the serum is 4.5 ng/ml or less, (2) Measurement value with FibroScan (manufactured by Echo-Sense Inc.), of which the principle is transient elastography that measures the propagation velocity of pulse oscillatory wave in the tissue with elasticity (kPa) by an ultrasonic pictorial analysis method as a noninvasive examination, is 9.0 kPa or less.

The glutathione in the present invention refers to a reduced glutathione or an oxidized glutathione or a mixture thereof. The reduced glutathione represents a tripeptide having a structure of γ-L-Glu-L-Cys-Gly, and the oxidized glutathione represents those obtained by binding of 2 molecules of the reduced glutathione via S—S bond. The form of glutathione may be any one as long as it contains glutathione as an active ingredient.

Glutathione of the present invention is not particularly limited as long as it is obtained with a method that can be used as a drug or food. Usually, glutathione of the present invention is produced by synthesis using a microorganism such as yeast, or oxygen, and the like.

A method for administering those containing glutathione as an active ingredient is not particularly limited, and may include oral administration and parental administration such as intravenous, intraperitoneal or subcutaneous administration. Specifically, the administration method may be any one of an oral agent such as a tablet, a powder, a granule, a pill, a suspension, an emulsion, an infusion or decoction, a capsule, a syrup, a solution, an elixir, an extract, a tincture and a liquid extract, or a parental agent such as an injection, a drop, a cream and a suppository.

Yeast containing glutathione can be also orally administered. As yeast containing a large amount of glutathione, there is "Hithion Cobo MG" (manufactured by KOHJIN Life Sciences Co., Ltd.), and as an yeast extract containing glutathione, there is "Hithion extract YH" (manufactured by KOHJIN Life Sciences Co., Ltd.) or the like.

The dose of the present invention is not particularly limited as long as it is an amount for expressing the functions described above. The dose and the administration number of times in the case of administration to human vary depending on the dosage form, the age or the body weight of a subject and the like. However, glutathione is administered usually 50 mg to 30 g, preferably 100 mg to 10 g, and particularly preferably 200 mg to 3 g once to several times per day for an adult.

The composition of the present invention can be taken not only as a drug, but also as functional food or nutritional supplementary food, and in such a case, the composition of the present invention may be taken in the intake amount of the previous paragraph.

EXAMPLES

Example 1

(Evaluation of Efficacy for NASH/NAFLD)

To subjects (16 persons) whose meal or exercise therapy for 12 weeks or more was ineffective and who had NAFLD in 31 IU/L or more of ALT, glutathione (manufactured by KOHJIN Life Sciences Co., Ltd.) was orally administered in 300 mg per one day. Liver biopsy was performed before initiation of glutathione administration and after 16 weeks of the administration, and blood examination was performed every 4 weeks. The results are shown in Table 1.

The effects of the present invention are summarized in Table 2 with the subjects affected with the present invention (Case IDs 1 to 9) and the subjects not affected with the present invention (Case IDs 10 to 16).

TABLE 1

| Case ID | Age | Sex | ALT (IU/L) | | | | | Type IV collagen 7s (ng/ml) | | | HbA1C (%) | | | | |
|---|---|---|---|---|---|---|---|---|---|---|---|---|---|---|---|
| | | | 0 wk | 4 wk | 8 wk | 12 wk | 16 wk | 0 wk | 8 wk | 16 wk | 0 wk | 4 wk | 8 wk | 12 wk | 16 wk |
| 1 | 39 | M | 67 | 77 | 39 | 43 | 48 | 4.3 | 3.9 | 4.3 | 5.2 | 5.3 | 5.1 | 5.4 | 5.3 |
| 2 | 71 | F | 96 | 35 | 34 | 23 | 50 | 4.9 | 4.9 | 4.9 | 5.8 | 6 | 5.9 | 6 | 6.1 |
| 3 | 39 | F | 61 | 48 | 37 | 32 | 43 | 3.1 | 2.9 | 3.4 | 6 | 6 | 6.1 | 6.1 | 6.2 |
| 4 | 41 | M | 96 | 24 | 19 | 20 | 25 | 4.7 | 4.4 | 3.9 | 5.4 | 5.2 | 5.3 | 5.3 | 5.3 |
| 5 | 45 | M | 63 | 46 | 31 | 38 | 42 | 3.4 | 3.6 | 3.6 | 3.8 | 3.7 | 3.8 | 3.8 | 3.8 |
| 6 | 41 | M | 76 | 62 | 65 | 59 | 94 | 3.4 | 3.4 | 3.4 | 5.4 | 5.5 | 5.7 | 5.9 | 5.8 |
| 7 | 31 | M | 193 | 133 | 138 | 125 | 135 | 4.4 | 4.3 | 4.9 | 5.3 | 5.3 | 5.2 | 5.3 | 5.3 |
| 8 | 55 | M | 59 | 34 | 33 | 34 | 44 | 4.5 | 4.5 | 4.6 | 5.8 | 5.7 | 5.8 | 5.9 | 5.9 |
| 9 | 45 | F | 97 | 87 | 81 | 60 | 93 | 3.7 | 3.7 | 3.7 | 5.4 | 5.3 | 5.4 | 5.4 | 5.4 |
| 10 | 64 | M | 97 | 90 | 77 | 72 | 86 | 5.3 | 4.8 | 4.9 | 6.9 | 6.8 | 6.7 | 6.9 | 7.4 |
| 11 | 60 | M | 69 | 51 | 53 | 54 | 63 | 4.4 | 4.9 | 4.4 | 6.9 | 7 | 7 | 7.4 | 7.4 |
| 12 | 61 | F | 66 | 60 | 52 | 59 | 64 | 6.5 | 6.7 | 6.9 | 8.9 | 9 | 8.9 | 8.5 | 8.3 |
| 13 | 46 | M | 91 | 96 | 73 | 76 | 86 | 7.7 | 7.4 | 7.4 | 7.1 | 6.9 | 7.1 | 7.4 | 7.5 |
| 14 | 74 | F | 47 | 53 | 65 | 48 | 63 | 4.8 | 4.6 | 4.4 | 6.2 | 6.4 | 6.6 | 6.5 | 6.4 |
| 15 | 64 | F | 33 | 30 | 37 | 32 | 27 | 4.4 | 4 | 3.3 | 7.8 | 7.6 | 7.6 | 7.8 | 7.6 |
| 16 | 66 | F | 48 | 45 | 41 | 40 | 40 | 5.6 | None | 4.8 | 7.1 | 7.2 | 7 | 6.9 | 7 |

| Case ID | Age | Sex | FibroScan (before treatment) | | FibroScan (after treatment) | |
|---|---|---|---|---|---|---|
| | | | CAP(dBe) | E (kPa) | CAP (dBe) | E (kPa) |
| 1 | 39 | M | 270 | 5.3 | 280 | 5.6 |
| 2 | 71 | F | 247 | 13.4 | 197 | 11.7 |
| 3 | 39 | F | 292 | 4.5 | 261 | 4.3 |
| 4 | 41 | M | 228 | 4.3 | 187 | 4.1 |
| 5 | 45 | M | 329 | 5.3 | 329 | 4.5 |
| 6 | 41 | M | 295 | 4.2 | 269 | 4.3 |
| 7 | 31 | M | 339 | 6.2 | 280 | 6.6 |
| 8 | 55 | M | 336 | 11.9 | 307 | 6.8 |
| 9 | 45 | F | 290 | 4.3 | 251 | 7.3 |
| 10 | 64 | M | 323 | 6.2 | 342 | 7.8 |
| 11 | 60 | M | 339 | 8.7 | 316 | 6.8 |
| 12 | 61 | F | Unmeasurable | | Unmeasurable | |
| 13 | 46 | M | 362 | 17.5 | 372 | 16.8 |
| 14 | 74 | F | 314 | 8.4 | 307 | 7.4 |
| 15 | 64 | F | 303 | 10.5 | 271 | 6.5 |
| 16 | 66 | F | 286 | 11.5 | 348 | 17.5 |

Case IDs 1 to 9 in Table 1 is a group in which ALT before initiation of the administration has improved by 20% or more after the administration. Meanwhile, in consideration of variation of the measurement, a case where there was a week at which ALT value after initiation after administration of the present invention improved by 20% or more in comparison to ALT value before the administration (0 wk), was considered to be effective. Next, results of comparison of various examination data before the administration of the present invention in the group affected with the present invention and the group not affected with the present invention are shown in Table 2.

TABLE 2

| Variable | Group not affected Before administration of present invention | Group affected Before administration of present invention | p value | |
|---|---|---|---|---|
| Age (years) | 57.7 ± 13.6 | 46.7 ± 11.9 | <0.0559 | NS |
| Gender (male:female) | 3:03 | 7:03 | <0.4255 | NS |
| Internal medicine history (Absence:Presence) | 0:06 | 5:05 | <0.0142 | # |
| Madical history (Absence:Presence) | 0:06 | 5:05 | <0.0142 | # |
| Hypertension (Absence:Presence) | 3:03 | 10:00 | <0.0076 | ## |
| Dyslipidemia (Absence:Presence) | 0:06 | 5:05 | <0.00142 | ## |
| Diabeteus mellitus (Absence:Presence) | 2:04 | 10:00 | <0.0013 | ## |
| Body weight (kg) | 70.2 ± 15.0 | 75.9 ± 11.7 | <0.7952 | NS |
| Body mass index (kg/m2) | 27.4 ± 4.4 | 27.3 ± 4.4 | <0.4793 | NS |
| AST (IU/L) | 53.5 ± 19.3 | 45.0 ± 19.3 | <0.2044 | NS |
| ALT (IU/L) | 57.8 ± 22.8 | 84.3 ± 39.6 | <0.9200 | NS |
| GGT (IU/L) | 63.2 ± 26.3 | 91.6 ± 67.0 | <0.8292 | NS |
| Ferritin (ng/mL) | 204.3 ± 209.9 | 224.0 ± 125.1 | <0.5920 | NS |
| Low density lipoprotein cholesterol (mg/dL) | 113.3 ± 24.6 | 133.3 ± 23.2 | <0.9372 | NS |
| High density lipoprotein cholesterol (mg/dL) | 53.3 ± 8.61 | 57.1 ± 14.9 | <0.5841 | NS |
| Triglyceride (mg/dL) | 211.3 ± 84.7 | 217.6 ± 195.5 | <0.5288 | NS |
| Free fatty acid (μEq/L) | 571.7 ± 267.8 | 704.0 ± 287.4 | <0.8188 | NS |
| Fastin plasma glucose (mg/dL) | 129.0 ± 57.6 | 102.8 ± 12.8 | <0.0899 | NS |
| Immunoreactive Insulin (μU/mL) | 15.5 ± 8.23 | 26.8 ± 27.1 | <0.8280 | NS |
| HbA1C (%) | 7.03 ± 1.25 | 5.50 ± 0.78 | <0.0043 | ## |
| Platelet count (/mL) | 23.0 ± 5.54 | 21.8 ± 3.38 | <0.3097 | NS |

TABLE 2-continued

| Variable | Group not affected Before administration of present invention | Group affected Before administration of present invention | p value | |
|---|---|---|---|---|
| Type IV collagen 7s | 5.40 ± 1.47 | 4.08 ± 0.63 | <0.0120 | # |
| CAP | 329.2 ± 35.5 | 300.5 ± 42.7 | <0.0948 | NS |
| Elastography | 11.3 ± 6.22 | 6.81 ± 3.38 | <0.0412 | # |

, P < 0.05
, P < 0.01

Example 2

Effects of the present invention were further confirmed using a mouse.

Mice (C57/B6J, 8 weeks old male) were divided into 4 groups (5 animals each), and the first group (DB) was freely fed with ordinary food (Certified Diet "MF" manufactured by Oriental Yeast Co., ltd.). The second group (HFD) was freely fed with high-fat food (High Fat Diet 32, manufactured by CLEA Japan, Inc.), was freely given water only. The third group (HFD6) was freely fed with high-fat food (High Fat Diet 32, manufactured by CLEA Japan, Inc.), and glutathione was mixed with water so that glutathione can be taken by 6 mg/kg/day. The fourth group (HFD60) was freely fed with high-fat food (High Fat Diet 32, manufactured by CLEA Japan, Inc.), and glutathione was mixed with water so that glutathione can be taken by 60 mg/kg/day.

When the mouse was 20 weeks old, the body weight, the liver weight, the serum aspartate aminotransferase (AST), the alanine aminotransferase (ALT), the serum triglyceride (TG), the free fatty acid value (FFA) and the total cholesterol value (T-cho) were measured.

Figure 2:
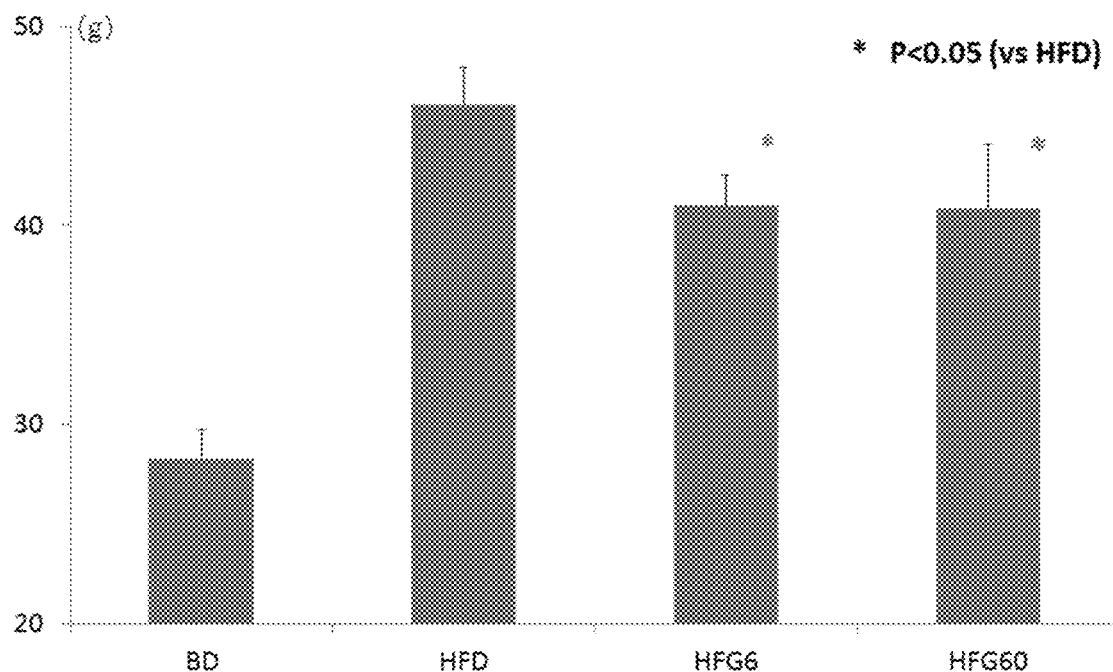
Figure 3A:
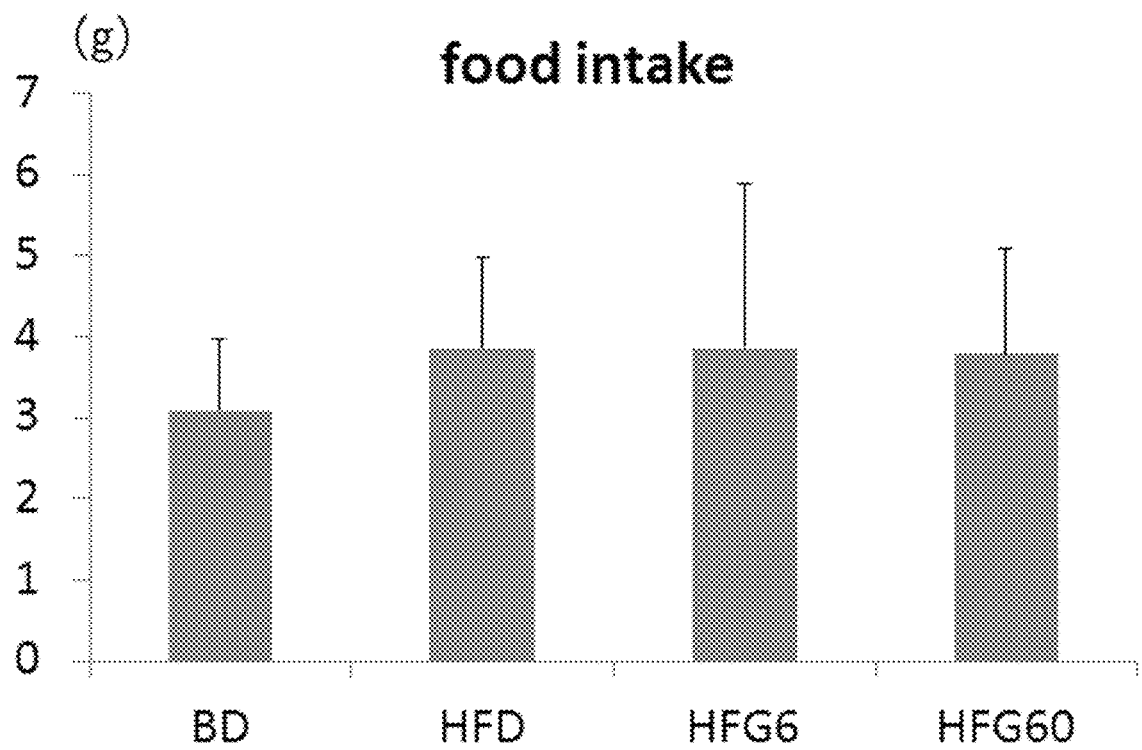
Figure 3B:
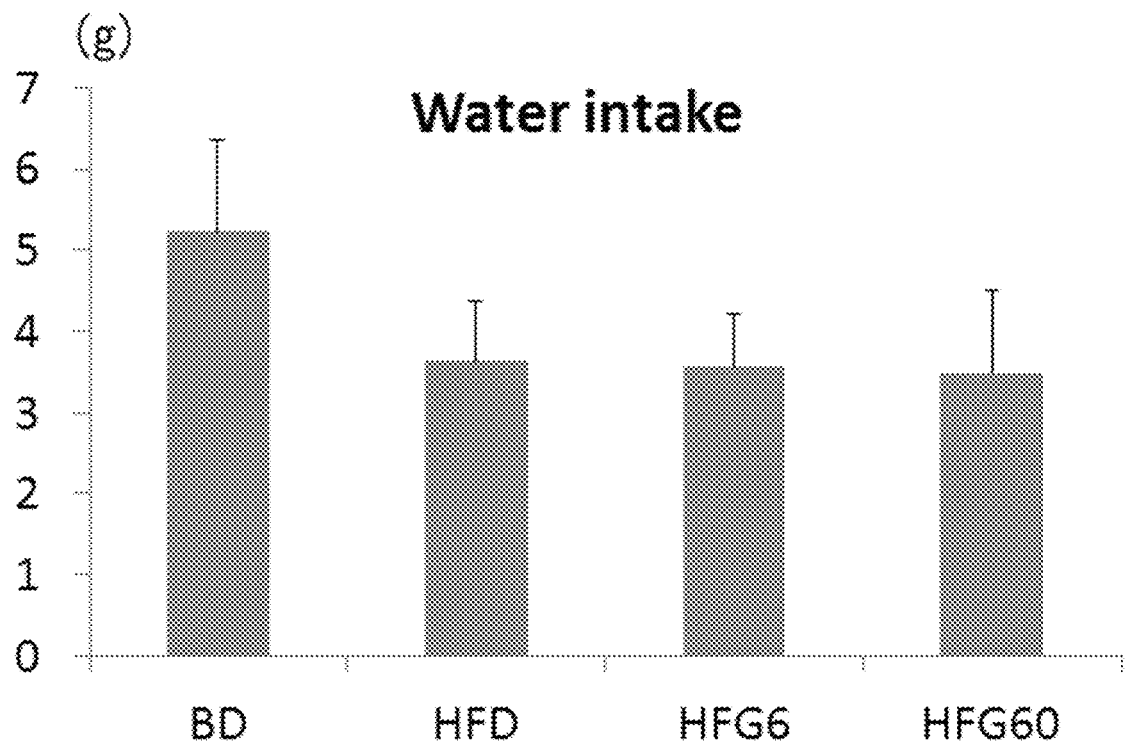
Figure 4A:
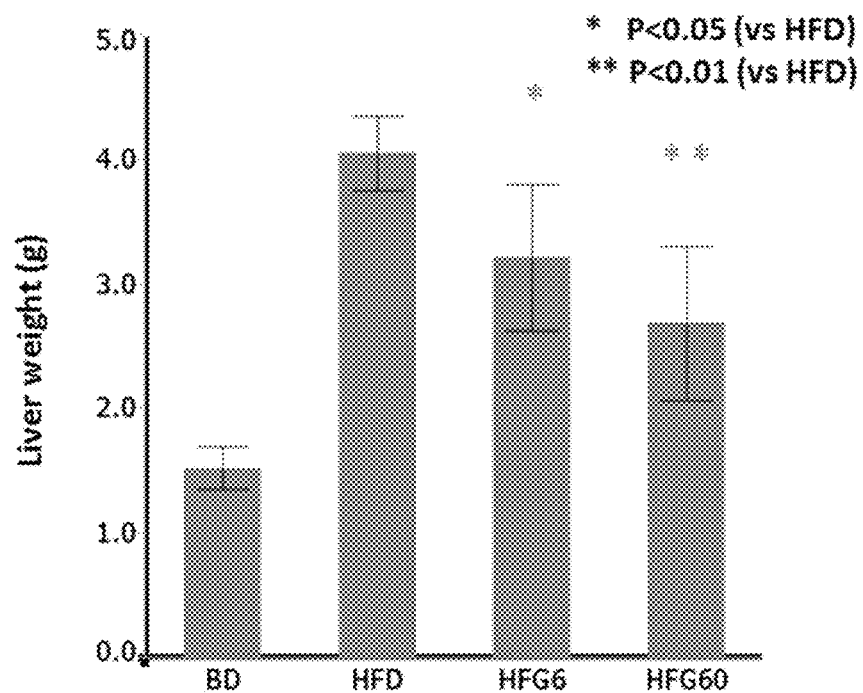
Figure 4B:
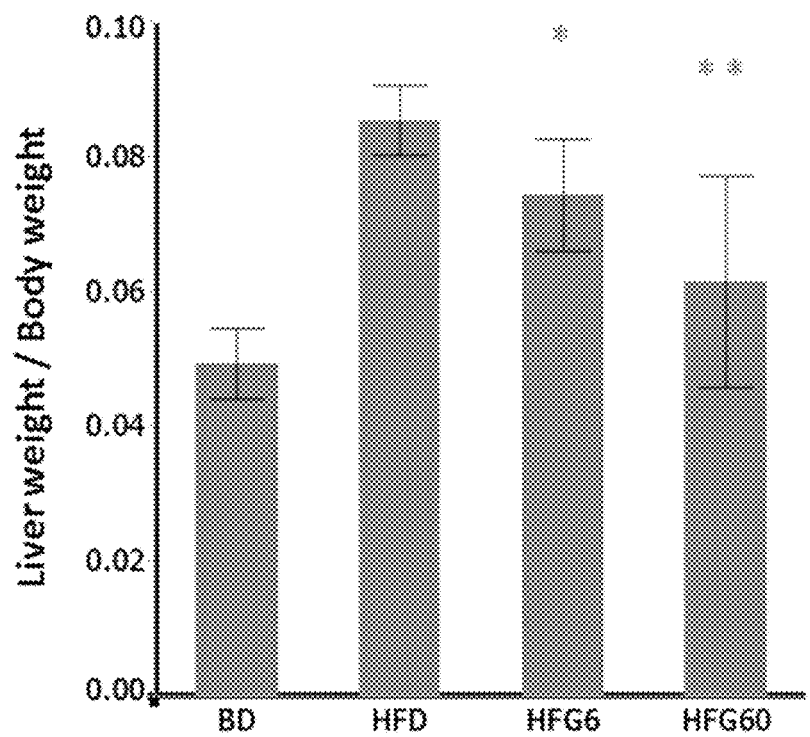

The results of the body weight and liver weight are shown in FIGS. 1 and 2. Furthermore, the consumption amounts of feed and water are shown in FIGS. 3A and 3B, respectively. There was no significant difference in the consumption amounts of feed and water in all of the groups. In the administration group of the present invention, decrease of the body weight was recognized. Furthermore, as shown in FIGS. 4A and 4B, the liver weight decreased dependently on the concentration of the present invention, and decrease of the body weight ratio was also recognized. It was found from this that deposition of fat on the liver by high-fat food was suppressed.

Figure 5A:
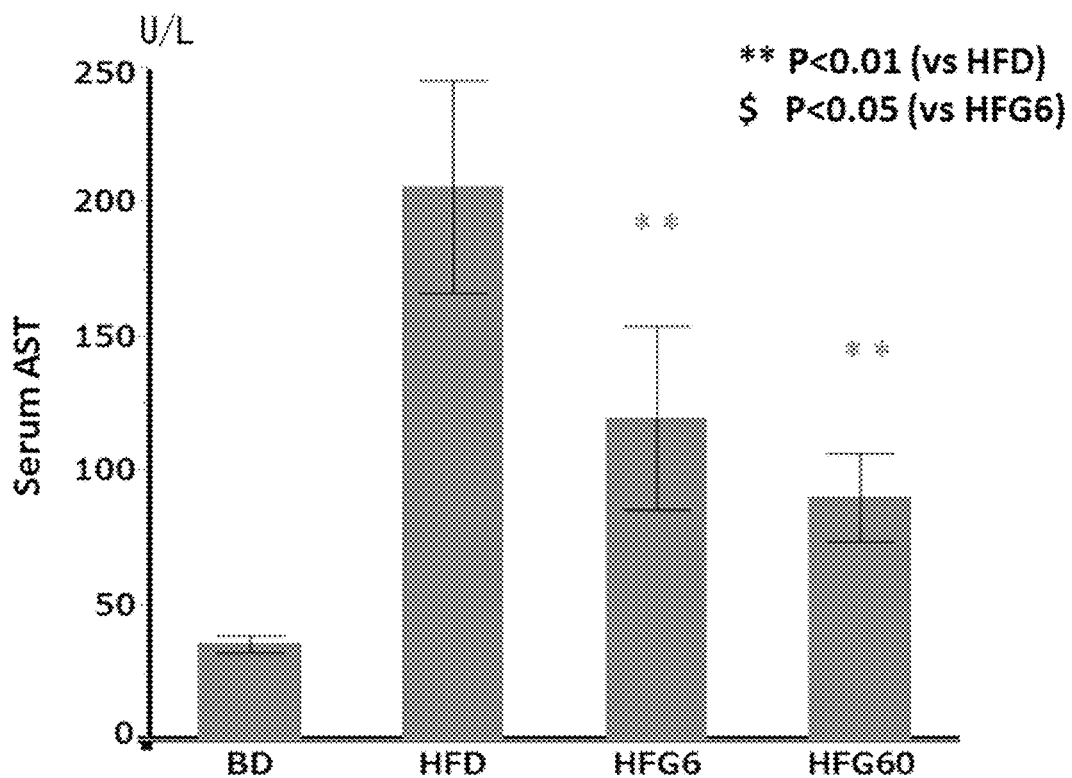
Figure 5B:
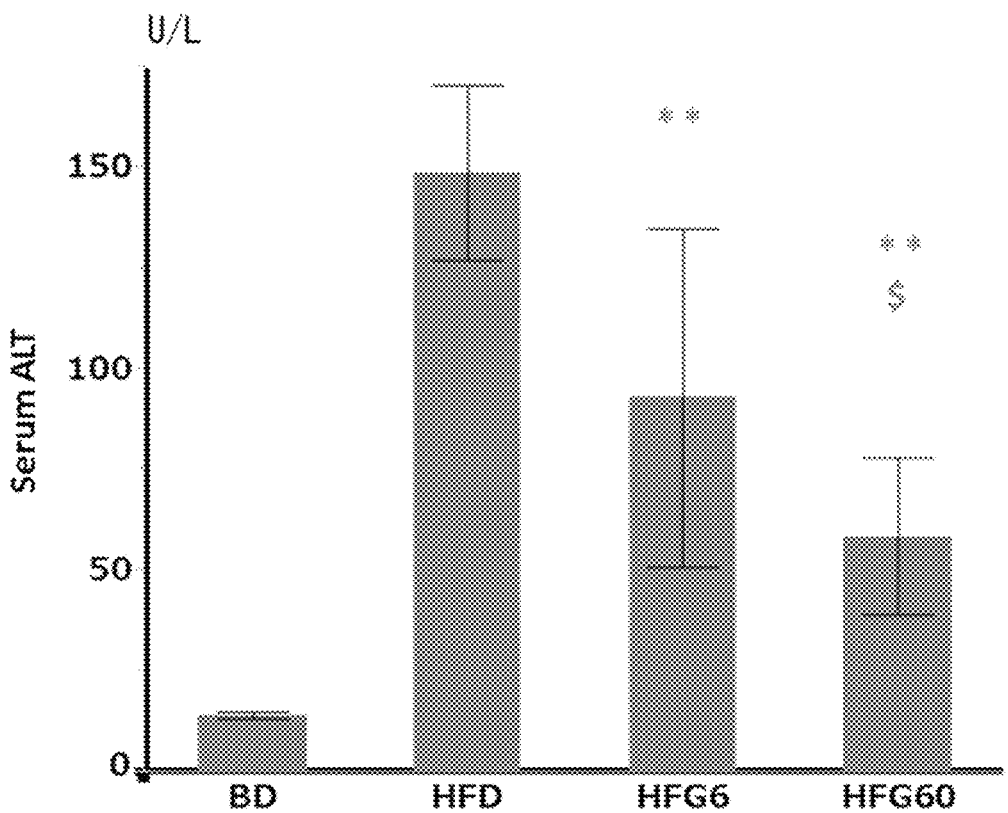
Figure 6B:
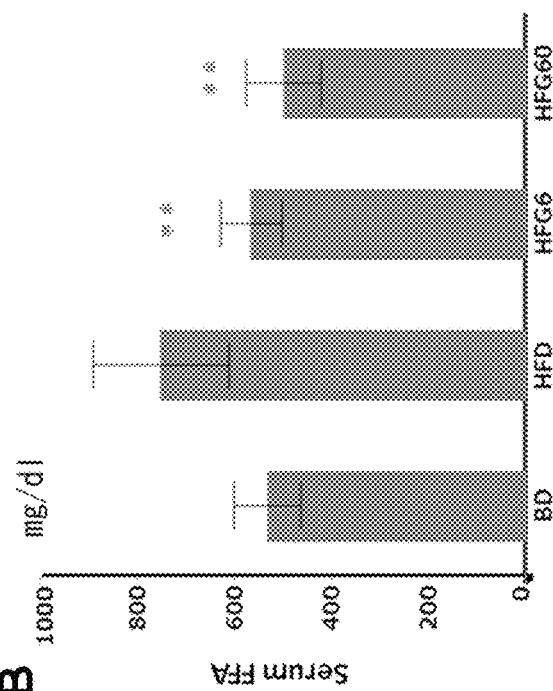
Figure 6A:
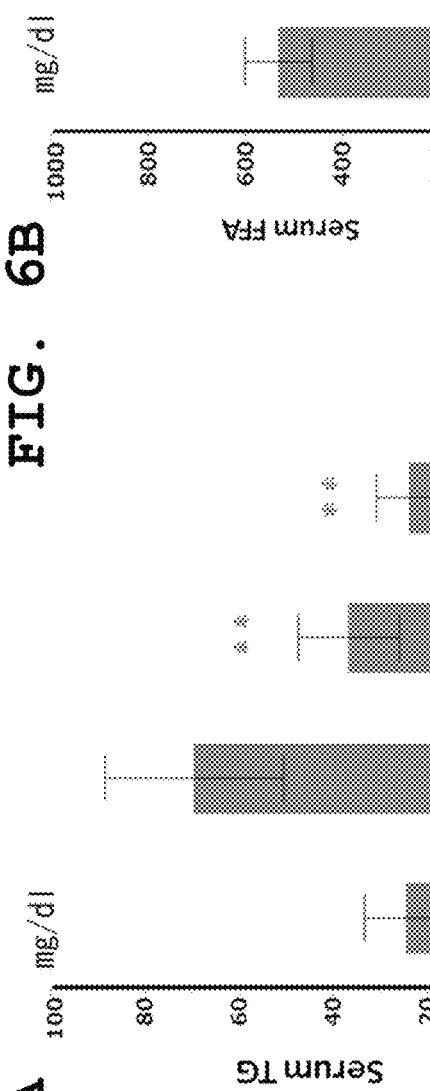
Figure 6C:
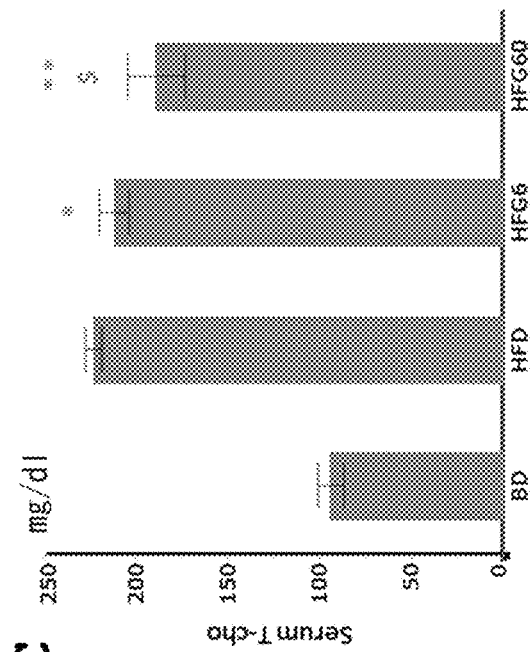

FIGS. 5A and 5B show the results of the serum AST and the serum ALT, respectively, and FIGS. 6A, 6B, and 6C show TG (triglyceride value), FFA (free fatty acid value), and T-cho (total cholesterol value), respectively. There were a significant decrease in the HFD6 group and the HFD60 group in comparison to the HFD group. In addition, when the HDF6 group and the HFD60 group were compared, there was recognized a decrease dependently on the concentration of the product of the present invention.

Efficacy for nonalcoholic fatty liver by administration of the product of the present invention was also confirmed in a mouse. With the mouse model of Example 2, influence on the liver by high-fat food intake only can be confirmed, and thus the effects of the product of the present invention in Example 1 could be observed.

From the results of the present Examples, the present invention is particularly effective for improving the nonalcoholic fatty liver disease in a case where the abnormality of a metabolic disorder (high blood pressure, diabetes, lipid abnormality) is mild or absent, in a case where medical history or internal medicine history is absent, in a case where liver stiffness is low (determined by the numerical value of elastography or Type IV collagen), or in a case where diabetes is not complicated (determined from the ratio of glycosylated hemoglobin).

FIG. 1 is a graph showing progress of body weight.
FIG. 2 is a graph showing body weight at 20 weeks old.
FIG. 3A is a graph showing intake amounts of feed.
FIG. 3B is a graph showing intake amounts of water.
FIG. 4A is a graph showing the liver weight.
FIG. 4B is a graph showing the ratio of liver weight/body weight.
FIG. 5A is a graph showing serum AST levels.
FIG. 5B is a graph showing serum ALT levels.
FIG. 6A is a graph showing serum TG (triglyceride value).
FIG. 6B is a graph showing serum FFA (free fatty acid value).
FIG. 6C is a graph showing serum T-cho (total cholesterol value).

The invention claimed is:

1. A method for improving a nonalcoholic fatty liver disease, comprising
    administering a composition comprising glutathione as an active ingredient to a patient in need of treatment of the nonalcoholic fatty liver disease,
    wherein the nonalcoholic fatty liver disease is a disease having low liver stiffness corresponding to any one of the following:
    (1) measurement value of Type IV collagen 7S domain in the serum is 4.5 ng/ml or less, or
    (2) measurement value with a device in which the principle is transient elastography that measures the propagation velocity of pulse oscillatory wave in the tissue with elasticity (kPa) by an ultrasonic pictorial analysis method as a noninvasive examination is 9.0 kPa or less, and
    an alanine aminotransferase (ALT) value after the composition is administered improved by 20% or more as compared to an alanine aminotransferase (ALT) value before the composition is administered.

2. The method of claim 1, wherein the disease having low liver stiffness corresponds to the measurement value of Type IV collagen 7S domain in the serum is 4.5 ng/ml or less.

3. The method of claim 1, wherein deposition of fat on a liver was suppressed in a treated patient as compared to an untreated patient.

4. The method of claim 1, wherein the patient has a glycosylated hemoglobin of 6.5% or more, and the patient is not treated for diabetes.

5. The method of claim 1, wherein the composition is administered orally.

* * * * *